(12) United States Patent
Cheung

(10) Patent No.: US 8,104,475 B2
(45) Date of Patent: Jan. 31, 2012

(54) MEDICAL TUBE ASSEMBLIES

(75) Inventor: Jazmine Minglai Cheung, Hythe (GB)

(73) Assignee: Smiths Group plc, London (GB)

( * ) Notice: Subject to any disclaimer, the term of this patent is extended or adjusted under 35 U.S.C. 154(b) by 689 days.

(21) Appl. No.: 12/289,819

(22) Filed: Nov. 5, 2008

(65) Prior Publication Data

US 2010/0108074 A1   May 6, 2010

(51) Int. Cl.
*A61M 16/00* (2006.01)
(52) U.S. Cl. .................................................. 128/207.14
(58) Field of Classification Search ........... 128/207.14–207.18; 604/264, 604/540
See application file for complete search history.

(56) References Cited

U.S. PATENT DOCUMENTS

| | | | |
|---|---|---|---|
| 3,169,529 A * | 2/1965 | Koenig | 128/207.14 |
| 4,315,505 A | 2/1982 | Crandall et al. | |
| 4,813,931 A * | 3/1989 | Hauze | 604/540 |
| 4,817,598 A * | 4/1989 | LaBombard | 128/207.14 |
| 5,119,811 A * | 6/1992 | Inglis et al. | 128/207.14 |
| 5,184,611 A * | 2/1993 | Turnbull | 128/207.14 |
| 5,386,826 A * | 2/1995 | Inglis et al. | 128/207.14 |
| 5,460,176 A * | 10/1995 | Frigger | 128/207.14 |
| 5,753,514 A * | 5/1998 | Karlsson et al. | 436/180 |
| 5,803,080 A * | 9/1998 | Freitag | 128/207.14 |
| 5,873,362 A * | 2/1999 | Parker | 128/207.14 |
| 5,964,785 A * | 10/1999 | Desecki et al. | 604/523 |
| 6,019,753 A * | 2/2000 | Pagan | 604/523 |
| 6,024,730 A * | 2/2000 | Pagan | 604/264 |
| 6,135,110 A * | 10/2000 | Roy | 128/207.15 |
| 2010/0108074 A1 * | 5/2010 | Cheung | 128/207.14 |
| 2010/0307488 A1 * | 12/2010 | Poulsen et al. | 128/200.26 |

FOREIGN PATENT DOCUMENTS

| | | |
|---|---|---|
| GB | 2056285 | 3/1981 |
| WO | 94/01156 | 1/1994 |
| WO | 2004/101048 | 11/2004 |

* cited by examiner

*Primary Examiner* — Stephen Crow
(74) *Attorney, Agent, or Firm* — Louis Woo

(57) ABSTRACT

A tracheostomy assembly has an outer tube and an inner cannula, the outer tube having a lip at its patient end to limit insertion of the inner cannula. The lip is formed with a recess or gap on the outside of the curve of the tube. This enables a suction catheter or similar device to be slid along the tube, after removal of the inner cannula, without the risk of catching on the lip.

7 Claims, 2 Drawing Sheets

MEDICAL TUBE ASSEMBLIES

BACKGROUND OF THE INVENTION

This invention relates to medical tube assemblies.

Tracheostomy tubes are inserted through a surgically-made opening in the throat so that one end of the tube locates in the trachea and the other end projects externally. Ventilation gas can then be supplied to the patient's airways via the tube or the patient can breath normally through the tube.

Tracheostomy tubes are often used where prolonged ventilation is required. In use, however, the inside of the tube becomes coated with secretions, which can reduce the flow of gas along the tube and provide a site for bacteria to multiply. Periodic removal and replacement of the tube is relatively traumatic and uncomfortable for the patient, and must be carried out by surgical staff. It is, therefore, preferable to clean the tube, either by using a suction catheter inserted along the bore of the tube or, preferably, by using an inner cannula. Where an inner cannula is used, this is configured to form a close sliding fit within the tube extending along its entire length. The inner cannula remains in place during normal ventilation and, when secretions have built up, it is removed and replaced by a new inner cannula. This replacement procedure can be carried out regularly by nursing staff so provides an efficient and effective arrangement for maintaining effective ventilation and reducing the risk of respiratory infection. Examples of tracheostomy tube assemblies with an outer tube and an inner cannula are described in, for example, GB2056285, U.S. Pat. Nos. 4,315,505, 4,817,598, 5,119,811, 5,184,611, 5,386,826, 6,019,753, 6,135,110, GBO800112.5, WO94/01156 and WO04/101048.

There are, however, problems with inner cannulae. The cannulae do reduce the cross-sectional area of the effective passage through the tube so it is important for the wall thickness to be as small as possible and for the cannula to be a close sliding fit within the outer tube whilst allowing free insertion and removal. It is also important that the inner cannula does not buckle, or otherwise deform in a manner that would reduce gas flow, when inserted along the outer tube, which may not be smoothly curved. The inner cannula should extend along the entire length of the outer tube without projecting from its end and should preferably form an effective seal at the patient end to prevent seepage of material between the inner wall of the inner cannula and the outer wall of the inner cannula. It has been found that a most effective assembly can be provided if the patient end of the outer tube is formed with a shallow inturned lip, in the manner described in U.S. Pat. No. 4,315,515. The inner cannula is configured so that its patient end abuts the rear-facing surface of this lip. In this way, the lip prevents the inner cannula projecting beyond the outer tube and also helps improve the seal between the patient end of the inner cannula and outer tube. One problem, however, with this arrangement is that when the inner cannula has been removed and a suction catheter or other elongate device is inserted through the outer tube to extend beyond the patient end of the outer tube, there is a tendency for the tip of the catheter or device to catch on the inturned lip at the patient end of the tube.

BRIEF SUMMARY OF THE INVENTION

It is an object of the present invention to provide an alternative medical tube assembly.

According to one aspect of the present invention there is provided a medical tube assembly comprising an outer tube and an inner cannula that is insertable and removable from the outer tube, the outer tube having, in use, a curve or bend along a part at least of its length and an internally-projecting lip towards its patient end adapted to limit insertion of the inner cannula, the lip being provided with a recess located at the outside of the curve of the tube such that, when the inner cannula is not in place, an elongate device can be inserted along the outer tube and slide through the recess beyond the patient end of the outer tube without catching on the lip.

According to another aspect of the present invention there is provided a medical tube assembly comprising: an outer tube; an inner cannula and a suction catheter, the inner cannula being insertable and removable from the outer tube, the outer tube having, in use, a curve or bend along a part at least of its length, a patient end, a machine end and an internally-projecting lip towards its patient end adapted to limit insertion of the inner cannula, the lip being provided with a recess located at an outside of the curve of the tube such that, when the inner cannula is not in place, the suction catheter can be inserted along the outer tube and slide through the recess beyond the patient end of the outer tube without catching on the lip.

According to a third aspect of the present invention there is provided a tracheostomy tube assembly comprising: an outer tracheostomy tube and an inner cannula, the inner cannula being insertable and removable from the outer tube, the outer tube having, in use, a curve or bend along a part at least of its length, a patient end, a machine end and an internally-projecting lip towards its patient end adapted to limit insertion of the inner cannula, the lip being provided with a recess located at an outside of the curve of the tube such that, when the inner cannula is not in place, an elongate device can be inserted along the outer tube and slide through the recess beyond the patient end of the outer tube and into the trachea without catching on the lip.

According to a fourth aspect of the present invention there is provided a medical tube adapted to receive an inner cannula within it, the tube having, in use, a curve or bend along a part at least of its length, a patient end, a machine end and an internally-projecting lip towards its patient end adapted to limit insertion of the inner cannula, the lip being provided with a recess located at an outside of the curve of the tube such that, an elongate device can be inserted along the outer tube and slide through the recess beyond the patient end of the outer tube without catching on the lip.

According to a fifth aspect of the present invention there is provided a method of using a tracheostomy tube assembly comprising the steps of: inserting in a patient a tracheostomy tube assembly of the kind comprising an outer tracheostomy tube and an inner cannula, the outer tube having a patient end, a machine end and an internally-projecting lip towards its patient end adapted to limit insertion of the inner cannula, the lip being provided with a recess located adjacent the posterior surface of the trachea; enabling ventilation via the assembly; removing the inner cannula; inserting an elongate device along the outer tube to slide through the recess and extend beyond the patient end of the outer tube and into the trachea without catching on the lip; removing the elongate device; and inserting a new inner cannula.

The elongate device may be a suction catheter.

A tracheostomy tube assembly according to any one of the preceding claims will now be described, by way of example, with reference to the accompanying drawings.

DETAILED DESCRIPTION OF THE PREFERRED EMBODIMENT

Figure 1:
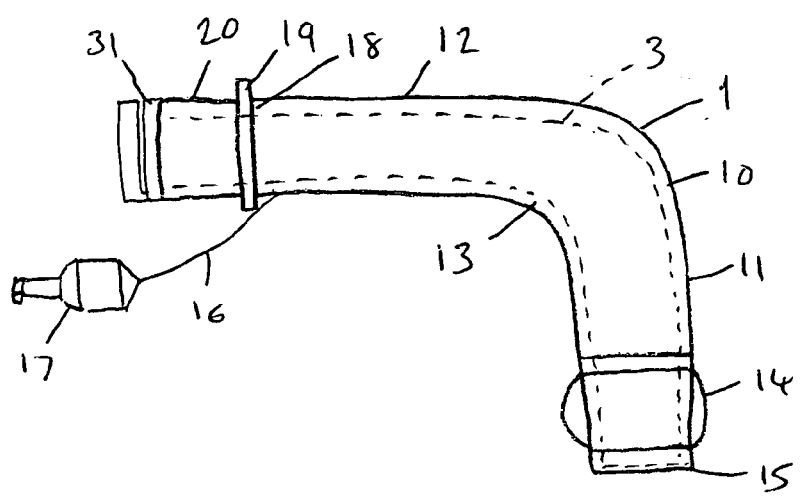
FIG. 1 shows the assembly schematically.

With reference first to FIG. 1, the tracheostomy tube assembly comprises an outer tube 1 and an inner tube or cannula 3, which is removable from the outer tube so that it can be periodically replaced in the usual way.

The outer tube 1 has a shaft 10 with straight forward or patient end section 11 and rear or machine end section 12 joined by a right-angle bend section 13. Alternatively, the outer tube could be smoothly curved along its entire length. In another embodiment the tube could have a natural straight shape and be highly flexible so that it could be bent during use to the shape of the anatomy. Such a flexible tube might be reinforced, such as by a helical wire reinforcement. The tube 1 typically has an external diameter of about 11.3 mm and an internal diameter of about 9.3 mm. A sealing cuff 14 embraces the shaft 10 close to its patient end 15; this can be inflated for sealing, or deflated for insertion and removal, via an inflation line 16 and a combined inflation indicator balloon and coupling 17. At its rear end 18, the outer tube 1 has a flange 19 to which a tape (not shown) can be attached for securing the assembly around the neck of the patient. A hub 20 projects from the machine side of the flange 19 by which gas connection can be made to the tube 1. In use, the tube 1 extends through a tracheostomy with the patient end 15 of the tube 1 located in the trachea. The cuff 14 is inflated to form a seal between the outside of the tube 1 and the tracheal wall so that gas flow is confined along the bore of the tube. The machine end 18 of the tube 1 extends externally of the tracheostomy. The patient end 15 differs from conventional tubes in a manner that will be described in detail later.

Figure 2:
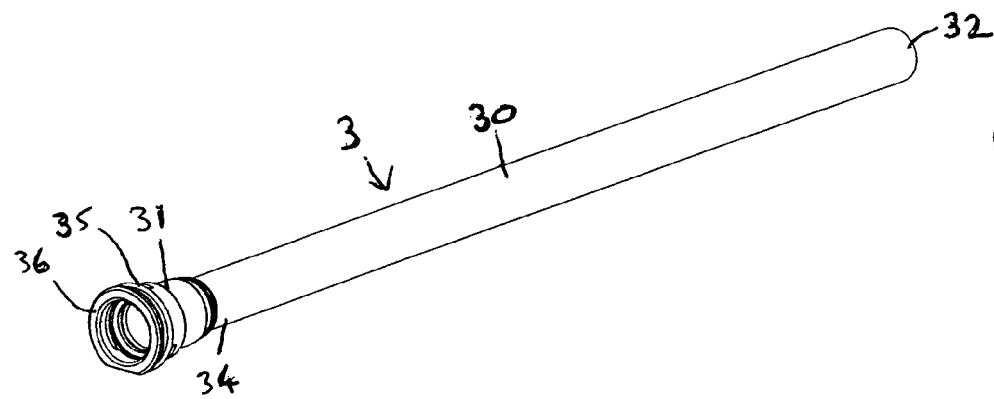
FIG. 2 is a perspective view of the inner cannula.
Figure 3:
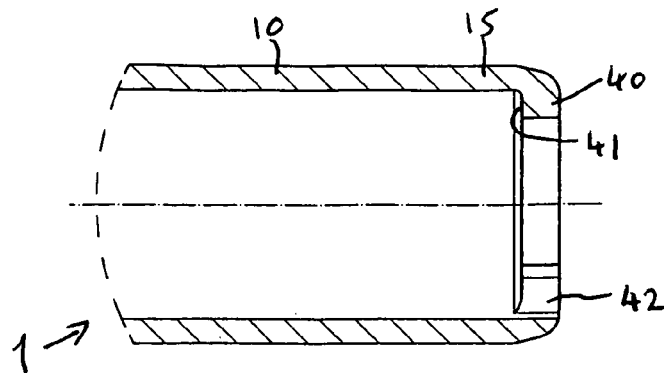
FIG. 3 is a cross-sectional side elevation view of the patient end of the outer tube to an enlarged scale.
Figure 4:
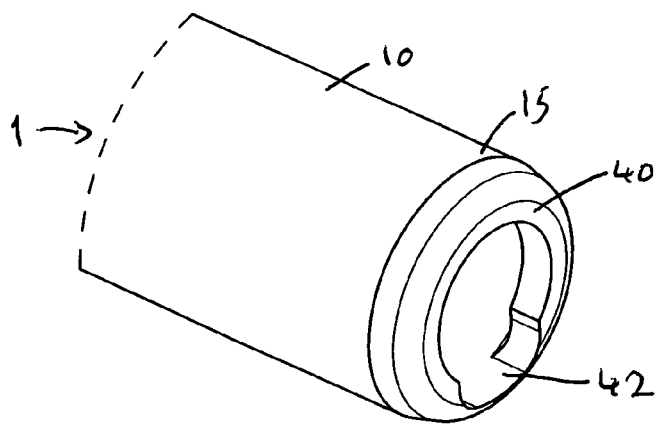
FIG. 4 is a perspective view of the patient end shown in FIG. 3.
Figure 5:
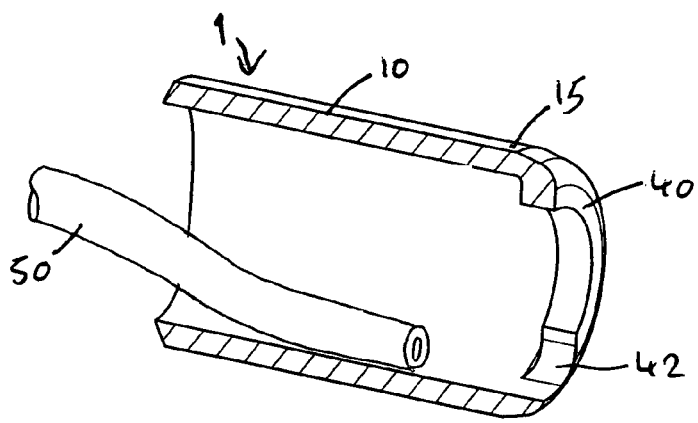
FIG. 5 is a cut-away perspective view of the patient end shown in FIGS. 3 and 4.
Figure 6:
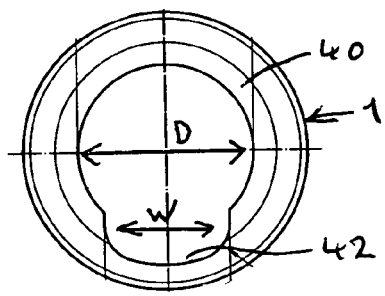
FIG. 6 is an end view of the patient end of the outer tube shown in FIGS. 3 to 5.

With reference now also to FIG. 2, the inner tube or cannula 3 comprises a shaft 30 and a machine end fitting 31. The inner cannula 3 is about 194 mm long and its shaft 30 has an internal diameter of about 8 mm and an external diameter of about 9 mm along the major part of its length. In use, the cannula 3 extends as a close sliding fit within the bore of the outer tube 1 with the patient end 32 of the cannula extending to the patient end 15 of the outer tube and with its end fitting 31 locating in the hub 20 of the outer tube. The shaft 30 is of ePTFE and is made by cutting from a length of extruded stock tubing. The nature of the shaft 30 is that it can flex readily to conform to the shape of the outer tube 1 without kinking as it is inserted. The shaft material has a very low coefficient of friction so that it can be inserted readily into the outer tube 1 as a close sliding fit without excessive axial compression forces being produced of a kind that could cause the shaft 30 to buckle. The shaft 30 is attached to a machine end fitting 31 in the manner described in detail in GB0800112.5 the contents of which are incorporated herein by reference.

With reference now to FIGS. 3 to 6, the patient end 15 of the outer tube 1 will be described in more detail. The patient end 15 of the outer tube 1 is moulded with an inturned, partannular lip 40, similar to the annular lip shown U.S. Pat. No. 4,315,515. The purpose of this lip 40 is to provide a rearfacing surface 41, which acts as a stop for the patient end 32 of the inner cannula 3 and thereby prevents it projecting from the patient end 15 of the outer tube 1. The lip 40 also helps, to some extent, to reduce seepage of material between the outside of the inner cannula 3 and the inside of the outer tube 1. The lip 40 does not form a complete annulus but is interrupted by a recess, notch or gap 42. This notch 42 is located on the outside of the bend of the outer tube 1 (that is, the outside of the bend of the tube during use) for a reason that will become apparent later. Typically, the width W of the notch is about 5 mm and the internal diameter D of the lip is about 7 mm. The width of the notch 42 is selected to provide a sufficient gap to allow a suction catheter 50 or other elongate device to be slid along the outer tube 1, after removal of the inner cannula 3, and to extend beyond the patient end 15 of the outer tube without catching on the lip 40. It will be appreciated, that, when a suction catheter 50 or the like is inserted within a curved tube, it will slide along the inner surface of the outer tube on the outside of its curvature or bend. It is for this reason that the notch 42 is located on the outside of the curve, that is, adjacent the posterior surface of the trachea in use. Although the notch 42 does expose a part of the region between the inner cannula 3 and outer tube 1, the risk of seepage is outweighed by the fact that the outer tube can be used easily with a suction catheter or the like. After suctioning in this way, a new inner cannula can be inserted in the outer tube.

It will be appreciated that the invention is not confined to tracheostomy tube assemblies but could be used in other tube assemblies of an outer and inner tube where an elongate device needs to be insertable freely beyond the patient end of the outer tube. The inner cannula could be of any different form.

What I claim is:

1. A medical tube assembly comprising: an outer tube and an inner cannula, the inner cannula being insertable and removable from the outer tube, the outer tube having, in use, a curve or bend along a part at least of its length, a patient end, a machine end and an internally-projecting lip towards its patient end adapted to limit insertion of the inner cannula, wherein the lip is provided with a recess located at an outside of the curve of the tube such that, when the inner cannula is not in place, an elongate device can be inserted along the outer tube and slide through the recess beyond the patient end of the outer tube without catching on the lip.

2. A medical tube assembly according to claim 1, wherein the elongate device is a suction catheter.

3. A medical tube assembly comprising: an outer tube; an inner cannula and a suction catheter, the inner cannula being insertable and removable from the outer tube, the outer tube having, in use, a curve or bend along a part at least of its length, a patient end, a machine end and an internally-projecting lip towards its patient end adapted to limit insertion of the inner cannula, wherein the lip is provided with a recess located at an outside of the curve of the tube such that, when the inner cannula is not in place, the suction catheter can be inserted along the outer tube and slide through the recess beyond the patient end of the outer tube without catching on the lip.

4. A tracheostomy tube assembly comprising: an outer tracheostomy tube and an inner cannula, the inner cannula being insertable and removable from the outer tube, the outer tube having, in use, a curve or bend along a part at least of its length, a patient end, a machine end and an internally-projecting lip towards its patient end adapted to limit insertion of the inner cannula, wherein the lip is provided with a recess located at an outside of the curve of the tube such that, when the inner cannula is not in place, an elongate device can be inserted along the outer tube and slide through the recess beyond the patient end of the outer tube and into the trachea without catching on the lip.

5. A medical tube adapted to receive an inner cannula within it, the tube having, in use, a curve or bend along a part at least of its length, a patient end, a machine end and an internally-projecting lip towards its patient end adapted to limit insertion of the inner cannula, wherein the lip is provided with a recess located at an outside of the curve of the tube such that, an elongate device can be inserted along the tube and slide through the recess beyond the patient end of the tube without catching on the lip when the inner cannula is not in place.

6. A method of using a tracheostomy tube assembly comprising the steps of: inserting in a patient a tracheostomy tube assembly of the kind comprising an outer tracheostomy tube and an inner cannula, the outer tube having a patient end, a machine end and an internally-projecting lip towards its patient end adapted to limit insertion of the inner cannula, the lip being provided with a recess located adjacent the posterior surface of the trachea; enabling ventilation via the assembly; removing the inner cannula; inserting an elongate device along the outer tube to slide through the recess and extend beyond the patient end of the outer tube and into the trachea without catching on the lip; removing the elongate device; and inserting a new inner cannula.

7. A method according to claim 6, wherein the elongate device is a suction catheter.

* * * * *